(12) United States Patent
Suh et al.

(10) Patent No.: US 9,158,134 B2
(45) Date of Patent: Oct. 13, 2015

(54) LIGHT-SENSITIVE COMPOUND, POLYMER POLYMERIZED WITH LIGHT-SENSITIVE COMPOUND AND PREPARATION METHOD THEREOF

(75) Inventors: Dong Hack Suh, Seongnam-si (KR); Won Jung Kim, Incheon-si (KR); Yun Cheol Yang, Gyeongsangnam-do (KR); Dong Wan Han, Uijeongbu-si (KR); Hong Jun Ahn, Seoul (KR); Jun Yong Hwang, Guri-si (KR); Kyung Mi Lee, Yongin-si (KR); Hyun Jin Lee, Siheung-si (KR); Seong Heun Cho, Yongin-si (KR); Ga Young Han, Suwon-si (KR)

(73) Assignee: INDUSTRY-UNIVERSITY COOPERATION FOUNDATION HANYANG UNIVERSITY (KR)

( * ) Notice: Subject to any disclaimer, the term of this patent is extended or adjusted under 35 U.S.C. 154(b) by 186 days.

(21) Appl. No.: 13/807,614

(22) PCT Filed: Jun. 30, 2010

(86) PCT No.: PCT/KR2010/004251
§ 371 (c)(1),
(2), (4) Date: Mar. 13, 2013

(87) PCT Pub. No.: WO2012/002590
PCT Pub. Date: Jan. 5, 2012

(65) Prior Publication Data
US 2013/0188120 A1    Jul. 25, 2013

(51) Int. Cl.
*C09B 29/00* (2006.01)
*G02F 1/00* (2006.01)
(Continued)

(52) U.S. Cl.
CPC ............ *G02F 1/0063* (2013.01); *C07C 245/08* (2013.01); *G02F 1/133788* (2013.01);
(Continued)

(58) Field of Classification Search
CPC .............. G02F 1/0063; G02F 1/13378; G02F 1/133788; G02F 1/133711; G03F 7/0045; C07C 245/08; Y10T 428/1005; Y10T 428/1036; Y10T 428/105
USPC ........... 428/1.1, 1.2, 1.26, 1.3, 1.33; 427/508, 427/520; 349/123, 124, 127; 524/555; 526/312; 534/851
See application file for complete search history.

(56) References Cited

U.S. PATENT DOCUMENTS

| | | |
|---|---|---|
| 2004/0209008 A1 | 10/2004 | Liang et al. |
| 2009/0274853 A1 | 11/2009 | Morishima |
| 2010/0134726 A1 | 6/2010 | Morishima et al. |

FOREIGN PATENT DOCUMENTS

| | | |
|---|---|---|
| WO | 2009/080147 A1 | 7/2009 |
| WO | 2009/080271 A1 | 7/2009 |

OTHER PUBLICATIONS

Okano et al "Azotolane Liquid Crystal Polymers", Nov. 9, 2006, JACS Communications, V128, p. 15368-15369.*

*Primary Examiner* — Ruiyun Zhang
(74) *Attorney, Agent, or Firm* — Volpe and Koenig, P.C.

(57) ABSTRACT

The present invention relates to a light-sensitive compound, a polymer formed by using the compound, and a production method of the compound and polymer. More particularly, the present invention relates to a unit compound that exhibits light-sensitivity with respect to three different wavelengths, a polymer having light-sensitive, which is polymerized by using the unit compound as a monomer, and a production method of the compound and polymer. The light-sensitive compound and the polymer according to the present invention may be usefully applied to an optical film.

21 Claims, 9 Drawing Sheets

(51) Int. Cl.
*C07C 245/08* (2006.01)
*G03F 7/004* (2006.01)
*G02F 1/1337* (2006.01)

(52) U.S. Cl.
CPC .......... *G03F 7/0045* (2013.01); *Y10T 428/1005* (2015.01); *Y10T 428/105* (2015.01); *Y10T 428/1023* (2015.01); *Y10T 428/1036* (2015.01)

LIGHT-SENSITIVE COMPOUND, POLYMER POLYMERIZED WITH LIGHT-SENSITIVE COMPOUND AND PREPARATION METHOD THEREOF

CROSS REFERENCE TO RELATED APPLICATION

This application is a 35 U.S.C. 371 National Stage Application of International Patent Application No. PCT/KR2010/004251, filed Jun. 30, 2010 which is incorporated by reference as if fully set forth.

FIELD OF INVENTION

The present invention relates to a light-sensitive compound and a polymer polymerized by using the compound as a monomer, and more particularly, to a compound which responds to light with various wavelengths to cause a structural change and is also capable of liquid crystal alignment and a polymer polymerized by using the compound as a monomer. The present invention also relates to a method for preparing the compound and the polymer.

BACKGROUND

Recently, display devices have been rapidly developed and among them, liquid crystal display devices may be representative display devices currently used.

A liquid crystal display device (LCD) is a display device that expresses pixels by using the principle of selectively penetrating light depending on the changes in polarization according to the arrangement of liquid crystal disposed between polarizing plates. However, when the display device is composed of only the liquid crystal and polarizing plates, there are problems in that brightness or contrast significantly deteriorates, light leakage occurs, and the like when a screen is observed not at the front surface thereof that is vertical to the screen but at different angles that deviate from the vertical.

In order to solve these problems, an optical compensation film such as a retardation film or a viewing angle compensation film is included in the polarizing plate along with a polarizer, or the retardation film, the viewing angle compensation film and the like are separately adhered to a display panel and then used. When an optical film such as a retardation film, a viewing angle compensation film and the like is inserted between a polarizing plate and a liquid crystal display element as described above, the color change of a liquid crystal display device (LCD) may be reduced and the viewing angle may be widened, thereby improving luminance.

The optical film in order to be used for the above-described use is mainly divided into a stretched film prepared by stretching a polymer film to give optical anisotropy and a liquid crystal film prepared by coating a polymeric liquid crystal compound on a plastic film substrate, drying the polymeric liquid crystal compound, and irradiating UV light thereon to cure the polymeric liquid crystal compound. The stretched film and liquid crystal film used as optical films have optical anisotropy, and particularly, the liquid crystal film may have various types of optical properties, which are difficult to be implemented by the stretched film.

That is, liquid crystal may be divided into a disc-type liquid crystal and a rod-type liquid crystal, depending on the shape of the liquid crystal molecules, and among them, the rod-type liquid crystal has various alignment forms such as planar, homeotropic, tilted, splay, cholesteric shapes and the like, and thus optical properties resulting from the various forms are also diverse and unique. Accordingly, various alignment characteristics of liquid crystal may be applied as they are by directly coating a polymeric liquid crystal compound on, for example, an acetyl cellulose substrate used as an optical film to use the acetyl cellulose substrate coated with the polymeric liquid crystal compound as an optical film, thereby obtaining an effect that is not implemented with only a protective film and a stretched film of a polarizer in polarizing plate, and serving as a role of an optical compensation film.

The above-described liquid crystal film (optical anisotropic film) is generally prepared by a method of coating an alignment film composition for forming a liquid crystal alignment film on a plastic substrate, drying and curing the composition to form an alignment film, rubbing the alignment film to give an alignment property, and then coating a polymeric liquid crystal compound thereon, drying and curing the polymeric liquid crystal compound to fix the compound. However, in the case of a method of forming an alignment film by the rubbing type as described above, there are difficulties in the preparation process due to drawbacks in the process. That is, in the alignment technology by the rubbing type in the related art, which is a kind of contact type, there are impurities and surface defects, and a washing process for removing impurities and surface defects is needed, thereby causing a problem in that the process is complicated and costs a lot.

In order to solve the problem, a technology in which an alignment property is intended to be given to an alignment film by using light has been developed as an attempt of a non-contact type. That is, in order to complement drawbacks of the rubbing process, a light alignment film that gives alignment characteristics to the alignment film in the non-contact type by using light have been currently developed to achieve process simplification, cost reduction and the like. For this purpose, there is need for a light controlling functional material that may control the changes in optical, chemical and physical characteristics caused by generating a structural change corresponding to light energy with various specific wavelengths.

SUMMARY

Thus, the present invention has been made to develop a compound having an optical alignment property, which may be applied to give an alignment property to an alignment film by using light, and a polymer using the compound, in order to reduce costs and obtain advantages in the process by overcoming disadvantages of the rubbing alignment in the related art.

In particular, the present invention is to provide a compound that may have selective photoreactivity with respect to three different wavelengths by preparing a compound that simultaneously has a chalcone group having photopolymerization characteristics and an arylazo group having photoisomerization characteristics, and a polymer using the same.

An object of the present invention is to provide a light-sensitive compound that may be reacted with light to change the structure thereof.

Another object of the present invention is to provide a polymer prepared by polymerizing the light-sensitive compound.

Still another object of the present invention is to provide an optical film in which the compound and the polymer are used. Yet another object of the present invention is to provide an optical film to which the compound and the polymer are applied as a light alignment film.

Still yet another object of the present invention is to provide a display device in which the compound and the polymer are used.

TECHNICAL SOLUTION

In order to achieve the above-described objects, the present invention provides an acrylic-based compound including a chalcone group having photopolymerization characteristics and an arylazo group having photoisomerization characteristics and including an alkyl chain at a terminal group such that the alignment of liquid crystals may be induced.

Specifically, the present invention provides a compound represented by the following Formula 1.

[Formula 1]

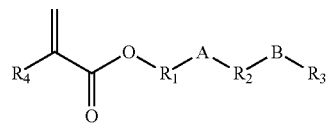

Here, each of "A" and "B" is one of a substituted or unsubstituted arylazo group and a substituted or unsubstituted chalcone group.

Further, in Formula 1, $R_1$, $R_2$ and $R_3$ may be the same as or different from each other and are each selected from the group consisting of an alkyl group having from 1 to 20 carbon atoms, an alkoxy group having from 1 to 20 carbon atoms, an aryl group and an alkyl ester group having from 1 to 20 carbon atoms, and $R_4$ is H or $CH_3$.

In the present invention, the substituted or unsubstituted arylazo group may be represented by the following Formula 2a.

[Formula 2a]

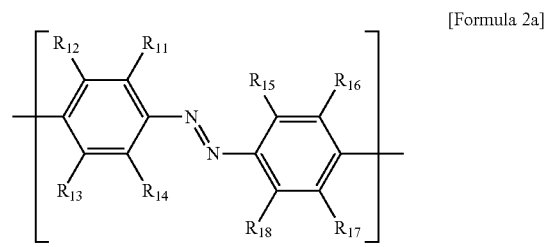

Here, $R_{11}$ to $R_{18}$ may be the same as or different from each other, and are each selected from the group consisting of hydrogen (H), an alkyl group having from 1 to 20 carbon atoms, an alkoxy group having from 1 to 20 carbon atoms, an aryl group and an alkyl ester group having from 1 to 20 carbon atoms.

According to an example of the present invention, azobenzene represented by the following Formula 2b may be applied as an example of the arylazo group.

[Formula 2b]

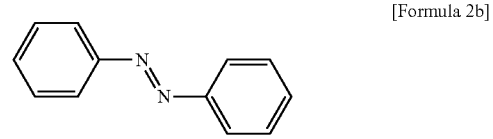 [SMILES: c1ccc(/N=N/c2ccccc2)cc1]

Meanwhile, the substituted or unsubstituted chalcone group may be represented by the following Formula 3a.

[Formula 3a]

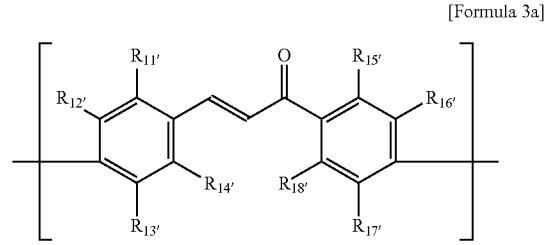

Here, $R_{11}'$ to $R_{18}'$ may be the same as or different from each other, and are each selected from the group consisting of hydrogen (H), an alkyl group having from 1 to 20 carbon atoms, an alkoxy group having from 1 to 20 carbon atoms, an aryl group and an alkyl ester group having from 1 to 20 carbon atoms. The substituent represented by Formula 3a does not have a left-right orientation at the connection site thereof, and the left and right of the substituent represented by Formula 3a may be reversed. Accordingly, the substituent represented by Formula 3a may be represented as follows.

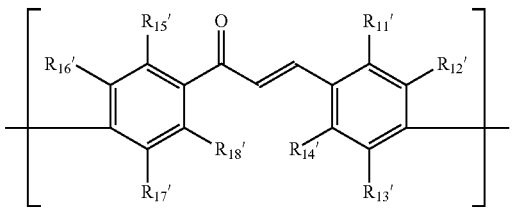

According to an example of the present invention, chalcone represented by the following Formula 3b may be applied as an example of the chalcone group.

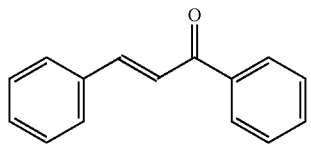

[Formula 3b]

As described above, according to an example of the present invention, each of A and B may be one of the substituents represented by Formula 2a and Formula 3a.

More specifically, each of A and B may be one of the azobenzene represented by Formula 2 and the chalcone represented by Formula 3.

That is, according to an example of the present invention, A may be the azobenzene represented by Formula 2 and B may be the chalcone represented by Formula 3. According to another example of the present invention, A may also be the chalcone represented by Formula 3 and B may also be the azobenzene represented by Formula 2 by reversing A and B.

According to an example of the present invention, the compound represented by Formula 1 may be a compound represented by the following Formula 4 or the following Formula 5.

[Formula 4]

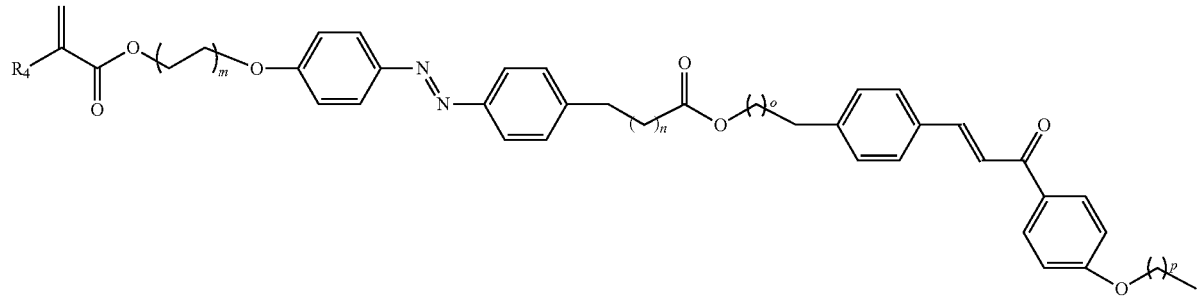

[Formula 5]

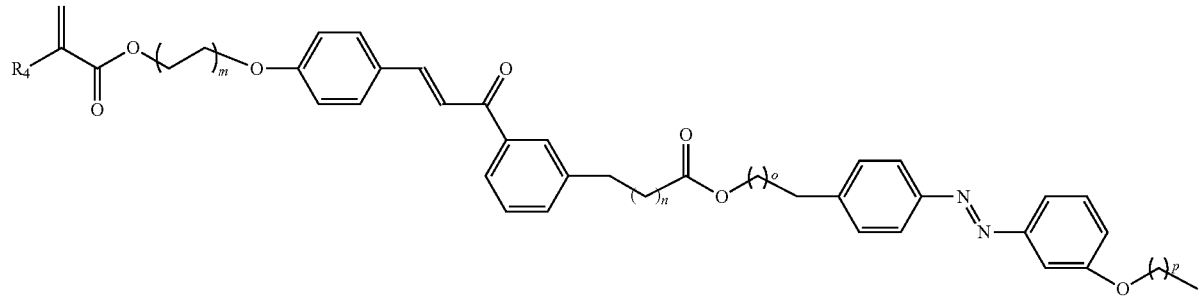

Here, m, n, o and p are each an integer from 1 to 5, and $R_4$ is H or $CH_3$.

Meanwhile, as an example of a compound in which in Formula 1, A is azobenzene and B is chalcone, there are compounds represented by the following Formulas 6a and 6b.

[Formula 6a]

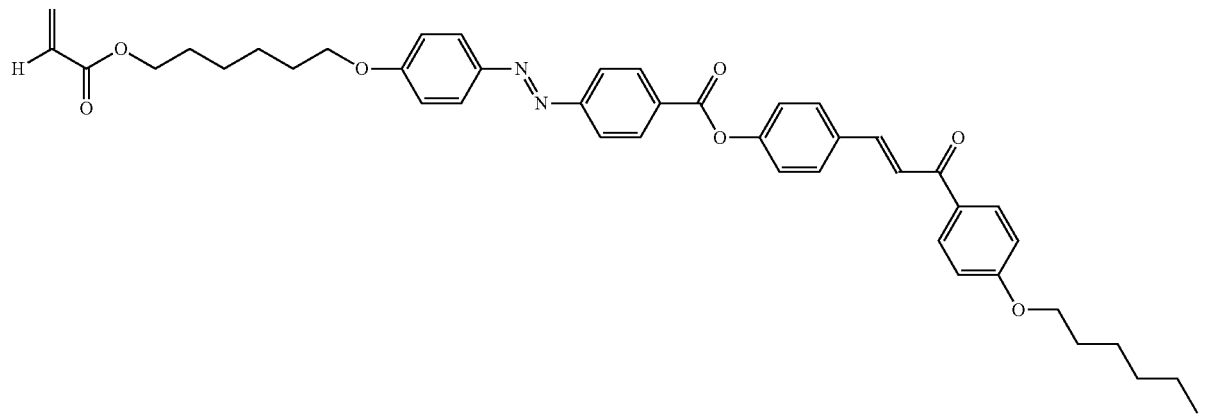

[Formula 6b]

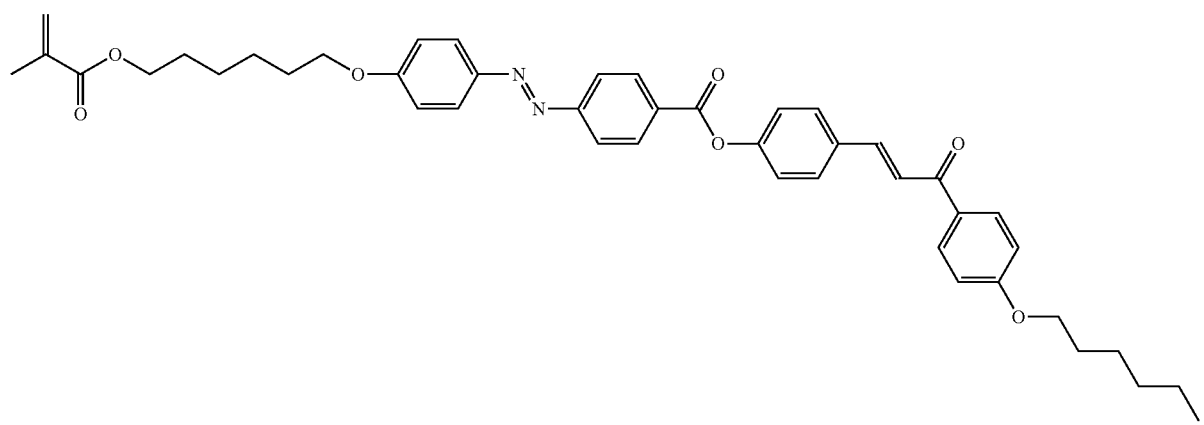

The compound represented by Formula 6a is 6-[4'-(4-hexyloxychalconyl benzoate azo)phenoxy]-hexylacrylate, and the compound represented by Formula 6b is 6-[4'-(4-hexyloxychalconyl benzoate azo)phenoxy]-hexylmethacrylate.

The compound of Formula 1 according to the present invention absorbs light having at least one of wavelengths from 280 nm to 340 nm, from 345 nm to 380 nm, and from 400 nm to 460 nm. As a result, the compound has light-sensitive characteristics.

Specifically, in the compound of Formula 1, cycloaddition may be generated by irradiation of light having a wavelength from 280 nm to 340 nm. In addition, the compound may be isomerized by irradiation of light having a wavelength from 345 nm to 380 or from 400 nm to 460 nm, and may be isomerized from the cis type to the trans type or from the trans type to the cis type.

The present invention provides a method for preparing the compound represented by Formula 1. As an example, the preparation method includes: reacting alkyl 4-aminobenzoate with phenol to prepare 4-hydroxy-4-alkoxycarbonyl azobenzol (Intermediate 1); reacting the 4-hydroxy-4-alkoxycarbonyl azobenzol with haloalkanol to prepare alkyl 4-[4-(6-hydroxyalkyl)phenylazo]benzoate (Intermediate 2); hydrolyzing the alkyl 4-[4-(6-hydroxyalkyl)phenylazo]benzoate to prepare 4-[4-(6-hydroxyalkoxy)phenylazo]benzoic acid (Intermediate 3); reacting the 4-[4-(6-hydroxyalkoxy)phenylazo]benzoic acid with methacrylic acid anhydride to prepare 6-[4-(4-benzoic acidazo)phenoxy]-alkylmethacrylate (Intermediate 4); reacting 4'-hydroxyacetophenone with haloalkane to prepare 4'-alkoxyacetophenone (Intermediate 5); reacting the 4'-alkoxyacetophenone with 4-alkoxybenzaldehyde to prepare 4-alkoxy-4'-alkoxychalcone (Intermediate 6); and reacting the 6-[4-(4-benzoic acidazo)phenoxy]-alkylmethacrylate (Intermediate 4) with the 4-alkoxy-4'-alkoxychalcone (Intermediate 6).

According to an example of the present invention, a method for preparing the compound represented by Formula 6b is provided, and the preparation method may include: reacting ethyl 4-aminobenzoate with phenol to prepare 4-hydroxy-4-ethoxycarbonyl azobenzol (Intermediate 1); reacting the 4-hydroxy-4-ethoxycarbonyl azobenzol with 1-cholo-6-hexenol to prepare ethyl 4-[4-(6-hydroxyhexyl)phenylazo]benzoate (Intermediate 2); hydrolyzing the ethyl 4-[4-(6-hydroxyhexyl)phenylazo]benzoate to prepare 4-[4-(6-hydroxyhexyloxy)phenylazo]benzoic acid (Intermediate 3); reacting the 4-[4-(6-hydroxyhexyloxy)phenylazo]benzoic acid with methacrylic acid anhydride to prepare 6-[4-(4-benzoic acidazo)phenoxy]-hexylmethacrylate (Intermediate 4); reacting 4'-hydroxyacetophenone with 1-bromohexane to prepare 4'-hexyloxyacetophenone (Intermediate 5); reacting the 4'-hexyloxyacetophenone with 4-hydroxybenzaldehyde to prepare 4-hydroxy-4'-hexyloxychalcone (Intermediate 6); and reacting the 6-[4-(4-benzoic acidazo)phenoxy]-hexylmethacrylate (Intermediate 4) with the 4-hydroxy-4'-hexyloxychalcone (Intermediate 6).

Here, the 4-hydroxy-4-ethoxycarbonyl azobenzol is referred to as Intermediate 1, the ethyl 4-[4-(6-hydroxyhexyl)phenylazo]benzoate is referred to as Intermediate 2, the 4-[4-(6-hydroxyhexyloxy)phenylazo]benzoic acid is referred to as Intermediate 3, the 6-[4-(4-benzoic acidazo)phenoxy]-hexylmethacrylate is referred to as Intermediate 4, the 4'-hexyloxyacetophenone is referred to as Intermediate 5, and the 4-hydroxy-4'-hexyloxychalcone is referred to as Intermediate 6.

The present invention also provides a polymer polymerized by using a monomer including the compound represented by Formula 1. That is, the present invention provides a polymer formed by polymerizing a monomer including the compound represented by Formula 1.

According to an example of the present invention, the monomer may further include at least one or more of acrylic acid, methacrylic acid, acrylonitrile, and styrene.

The polymer according to the present invention may be a homopolymer type formed by a single monomer, and a copolymer type formed by two or more monomers.

According to an example of the present invention, the polymer may have a molecular weight from 3,000 to 300,000.

According to an example of the present invention, there is a polymer represented by the following Formula 7 as a homopolymer formed by polymerizing the compound represented by Formula 1.

[Formula 7]

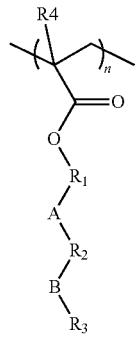

Here, A, B and $R_1$ to $R_4$ are the same as those as defined above, and n is an integer from 5 to 500. According to another example of the present invention, n may also be an integer from 10 to 300. The polymer may have a molecular weight from about 3,000 to about 300,000, and according to another example of the present invention, the molecular weight may also be from about 5,000 to about 200,000.

As an example of the polymer represented by Formula 7, there is a polymer represented by the following Formula 8.

[Formula 8]

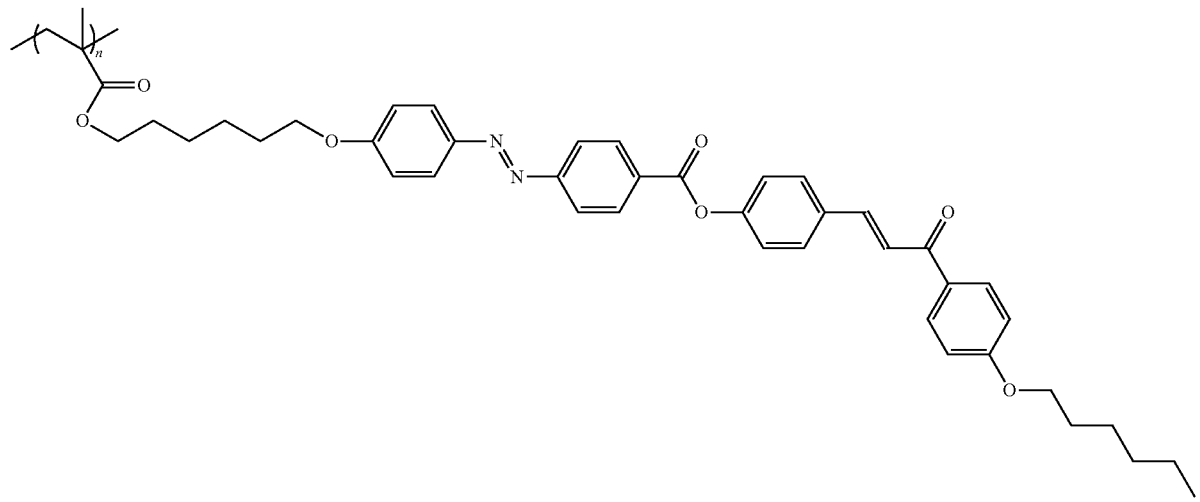

Here, n is an integer from 5 to 500.

The compound represented by Formula 1 may be represented as various forms according to the kind of A, B and $R_1$ to $R_3$. Accordingly, when two or more compounds which are represented by Formula 1 but different from each other are used as monomers, a copolymer is prepared.

As a polymer in which the compound represented by Formula 1 is used as a monomer, there is a polymer represented by the following Formula 9, which is an example of copolymers prepared by polymerizing monomers in which two or more compounds different from each other are mixed.

[Formula 9]

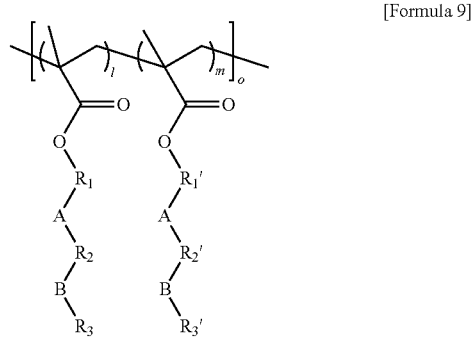

Here, l and m are an integer from 1 to 100, and o is an integer from 5 to 500. Furthermore, $R_1'$, $R_2'$ and $R_3'$ may be the same as or different from each other, and may be each selected from the group consisting of an alkyl group having from 1 to 20 carbon atoms, an alkoxy group having from 1 to 20 carbon atoms, an aryl group and an alkyl ester group having from 1 to 20 carbon atoms.

The copolymer may have a molecular weight from about 3,000 to about 300,000, and according to another example of the present invention, the polymer may have a molecular weight from about 5,000 to about 200,000.

In addition to the polymer represented by Formula 9, there are various copolymers polymerized by using various kinds of monomers. Those skilled in the art may prepare various kinds of copolymers by using various compounds, in which the kinds of A, B and $R_1$ to $R_3$ are diverse in Formula 1, as a monomer, if necessary.

For example, in addition to the compound represented by Formula 1 as a monomer, various copolymers may be prepared when the polymer is polymerized by further adding at least one or more of acrylic acid, methacrylic acid, acrylonitrile and styrene.

An example of the copolymer may be a polymer represented by the following Formula 10.

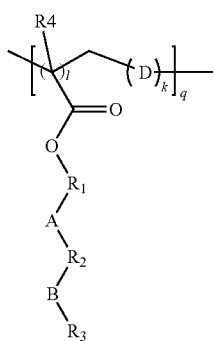

[Formula 10]

Here, A, B and $R_1$ to $R_4$ are the same as those as defined above, and D is at least one selected from the group consisting of methyl acrylate (MA), methyl methacrylate (MMA), acrylonitrile and styrene. Further, l and k are an integer from 1 to 100, and q is an integer from 5 to 500.

According to an example of the present invention, the method for preparing the polymer may include: mixing the compound of Formula 1 as a monomer with a polymerization initiator in a container and then adding a solvent thereto to dissolve the compound of Formula 1 and the polymerization initiator; sealing the container while removing gas therefrom; and polymerizing the compound of Formula 1 while maintaining the sealed container at a temperature from 70° C. to 100° C.

Here, the monomer may also be a compound consisting of a single kind, and may also be a compound consisting of two or more compounds different from each other. In addition, at least one or more of acrylic acid, methacrylic acid, acrylonitrile and styrene may be additionally mixed with the monomer consisting of the compound represented by Formula 1.

According to an example of the present invention, benzoyl peroxide (BPO), AIPN and the like may be used as the polymerization initiator.

According to an example of the present invention, any solvent may be used as the solvent as long as the organic solvent has solubility for a monomer such as benzene, a substituted phenyl-based compound or the like. Non-limiting examples of the solvent include benzene, toluene, xylene, para-xylene, meta-xylene, ortho-xylene and the like.

The compound represented by Formula 1 according to the present invention shows characteristics that the structure is isomerized from the cis-type to the trans-type, and vice versa by irradiation of light. The following Formula 11 represents only an aryl group moiety in which an N=N double bond is formed in the compound represented by Formula 1, showing an isomerization from trans- to cis-form, and vice versa.

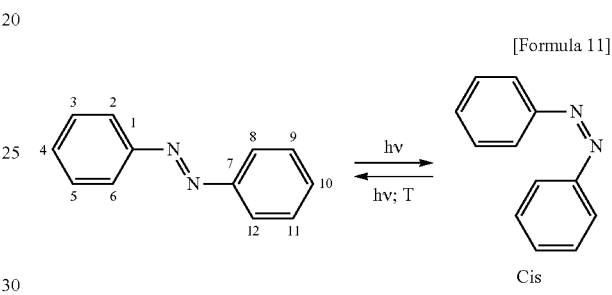

[Formula 11]

Specifically, an isomerization from cis- to trans-form is caused by irradiation of light having a wavelength from 345 nm to 380 nm, and an isomerization from trans- to cis-form is caused by irradiation of light having a wavelength from 400 nm to 460 nm.

As described above, the compound according to the present invention and the polymer prepared by using the same have light sensitivity in which the compounds are reacted by light energy.

In addition, the compound according to the present invention includes a carbon double bond at a chalcone group, and has optical characteristics caused thereby. Specifically, cycloaddition may be generated by irradiation of light having a wavelength from 280 nm to 340 nm. This is also referred to as the photocycloaddition by the 2π+2π bond, and the optical characteristics of chalcone may be described by the following Formula 12.

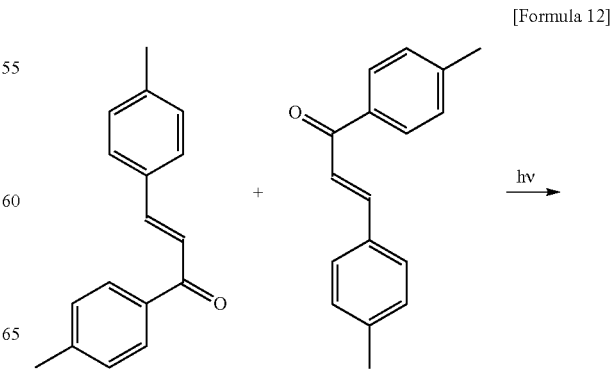

[Formula 12]

-continued

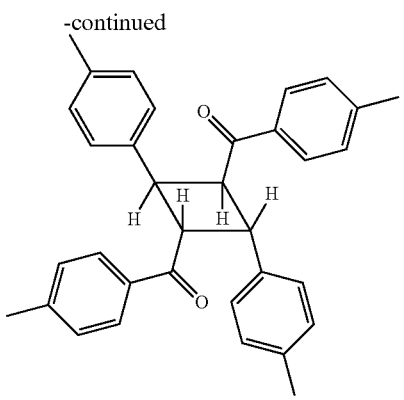

The compound according to the present invention has a photopolymerization functional group for light as described above and thus may show excellent characteristics such as chemical resistance, heat resistance, abrasion resistance and the like in the film state.

The present invention also provides an optical film coated with a polymer formed by polymerizing a monomer including the compound represented by Formula 1. According to an example of the present invention, the polymer forms an alignment film of the optical film.

Specifically, the present invention provides an optical film including: a film substrate; and a coating layer formed by coating a polymer prepared by using a monomer including the compound of Formula 1 on the surface of the film substrate.

Here, the film substrate may be selected from the group consisting of a polyacrylate (PA) film, a polymethylacrylate (PMA) film, a PMMA film, a PET film, a PC film, a PES film, a cyclic olefin compound (COC) film and a polyimide film.

The compound represented by Formula 1 according to the present invention and the polymer formed by polymerization of the compound have light-sensitive characteristics in which the arrangement thereof is changed by irradiation of light and thus may have orientation. Accordingly, the compound and the polymer according to the present invention may be usefully applied to an alignment film of the optical film.

Compounds applied to alignment films in the related art generally have light sensitivity for one or two wavelengths, whereas the compound represented by Formula 1 according to the present invention and the polymer formed by polymerizing the same have light sensitivity for three wavelengths and thus may be applied to various fields.

The present invention also provides a method for preparing an optical film, including: preparing a film substrate; coating the polymer according to the present invention on one side of the film substrate; and aligning the polymer by irradiating light.

According to an example of the present invention, in the aligning of the polymer, light having at least one of wavelengths from 280 nm to 340 nm, from 345 nm to 380 nm and from 400 nm to 460 nm may be irradiated.

Specifically, according to an example of the present invention, the optical film may be prepared by a method including: preparing a film to be used as a substrate; and coating the polymer according to the present invention on one side of the substrate formed of the film, and may be prepared by coating at least one of the polymers represented by Formulas 7 to 10 on the film to be used as a substrate.

In the above, the method further includes irradiating light such that the polymer has orientation. That is, when the polymer according to the present invention is first coated on the film substrate to form a coating layer, the coating layer may be aligned by irradiating light having a wavelength to allow the polymer to have a desired alignment to allow the polymer to have a certain alignment, and then curing the polymer.

When the polymer according to the present invention is used, light may be used to give alignment property, and thus the alignment property may be given by a non-contact type method. Impurities and surface defects may be reduced and processes may be simplified, compared to the rubbing alignment method that is a contact type method in the related art, thereby reducing costs.

The optical film shows optical characteristics and the kind thereof is not limited. Examples of the optical film include a retardation film, a viewing angle compensation film, a protective film and the like.

The present invention also provides a display device including the optical film. The kind of display device is not particularly limited. When the optical film according to the present invention is used in a display device, it is possible to select and control a pretilt angle defined as an angle between a substrate surface and liquid crystal molecules in a range of 3° or less for a horizontal alignment film and in a range of 80° or more for a vertical alignment film.

The compound and the polymer according to the present invention show characteristics of nematic thermotropic liquid crystal that has liquid crystal characteristics in response to heat, and thus the interaction with liquid crystal is excellent compared to compounds or polymers which are used in an alignment film in the related art. Furthermore, compounds which are not a polymer have liquid crystal characteristics alone and thus may be applied to various fields. Accordingly, the optical film according to the present invention may be usefully applied particularly to liquid crystal display devices (LCD).

Advantageous Effects

The compound represented by Formula 1 according to the present invention and the polymer polymerized by using the same have light sensitivity for three wavelengths and thus may be used in various application fields, and when the compound and the polymer according to the present invention are used, light may be used in a non-contact mode to give alignment property to an alignment film, and thus impurities and surface defects may be reduced and processes may be simplified, compared to the rubbing alignment mode in the related art, thereby reducing costs.

Further, the compound and the polymer according to the present invention show characteristics of nematic thermotropic liquid crystal that has liquid crystal characteristics in response to heat, and thus the interaction with liquid crystal is excellent compared to compounds or polymers which are used in an alignment film in the related art. In addition, compounds which are not a polymer have liquid crystal characteristics alone and thus may be applied to various fields.

Furthermore, the compound and the polymer according to the present invention have a photopolymerization functional group and thus chemical resistance, heat resistance, abrasion resistance and the like are excellent in the film state in which the compound and the polymer are applied.

DETAILED DESCRIPTION OF EMBODIMENTS

Hereinafter, the present invention will be described in more detail with reference to Examples.

Example 1

Preparation of Compound Represented by Formula 6b

Figure 1:
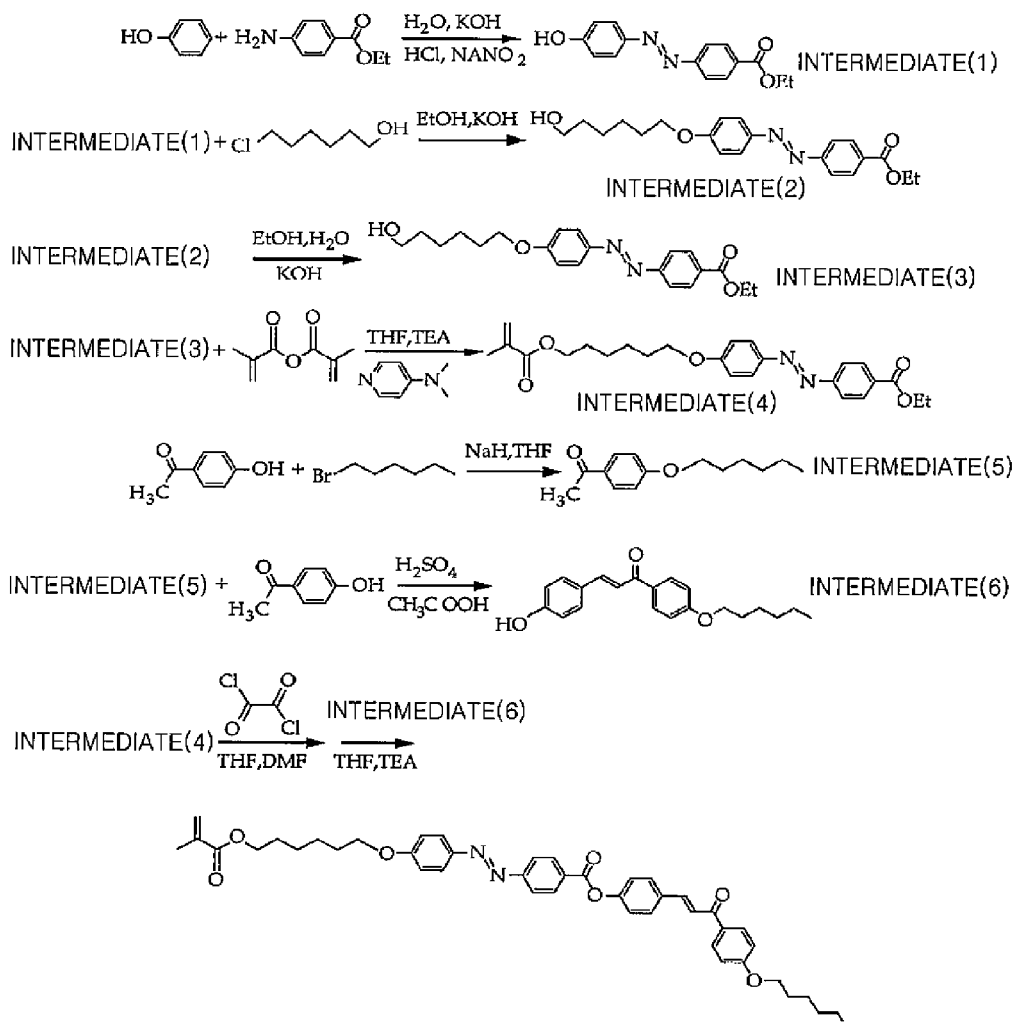
FIG. 1 is an overall scheme related to the synthesis of a compound represented by Formula 1.

The preparation process of the compound represented by Formula 6b may refer to FIG. 1. Hereinafter, the preparation process will be described in detail.

Synthesis of 4-hydroxy-4-ethoxycarbonyl azobenzol (Intermediate 1)

(1) Ethyl 4-aminobenzoate (10 g, 60.6 mmol) is dissolved in a 1 mol-hydrochloric acid solution (100 mL), and then stored in iced water at 0° C. to maintain the temperature.

(2) The solution in (1) is slowly added to an aqueous solution prepared by dissolving $NaNO_2$ (4.2 g, 60.8 mmol) in water (30 mL), and then the mixture is stirred for 30 minutes.

(3) NaOH (7.2 g, 0.18 mol) and phenol (5.8 g, 61.7 mmol) are dissolved in water (80 mL), the solution is stirred at 0° C. for 30 minutes, and then the aqueous solution in (2) is slowly added thereto. Thereafter, the mixed aqueous solution is stirred for 1 hour while maintaining the temperature at 0° C.

Figure 2:
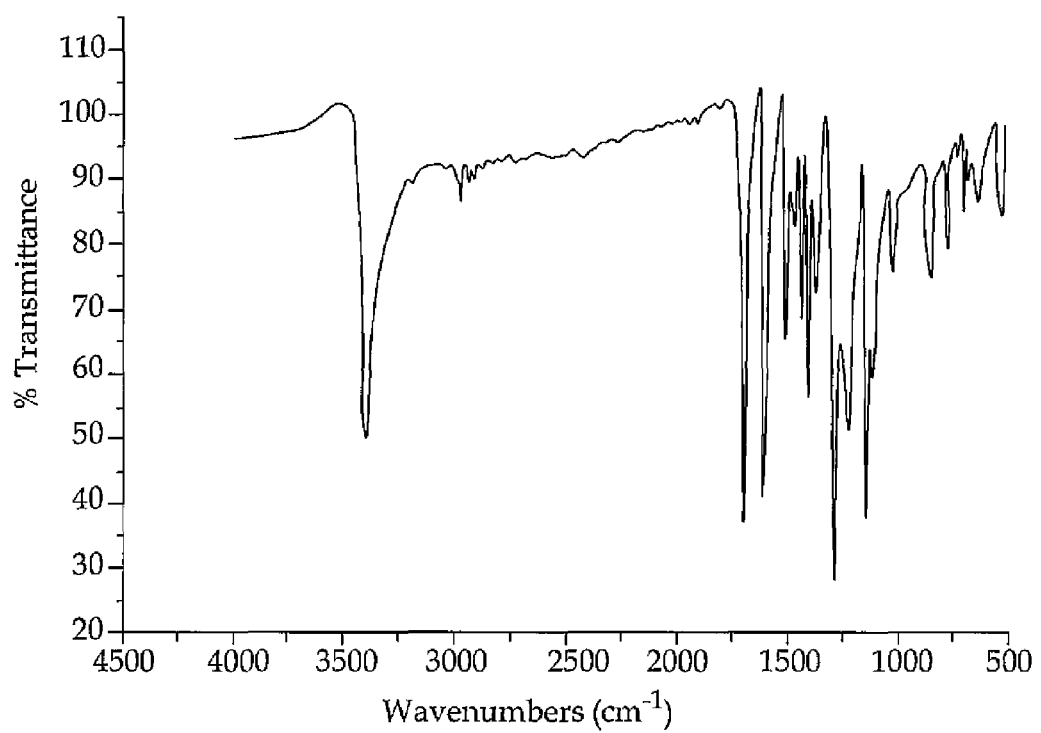
FIG. 2 is an FT-IR spectrum of Intermediate 1.

(4) The mixture mixed above is poured into water to dilute the mixture, and then the aqueous solution is neutralized with a 5% hydrochloric acid to perform precipitation. A precipitate is obtained by a reduced-pressure filtration method, and then is recrystallized twice from ethanol to obtain Intermediate 1 which is a red crystal. (11.8 g, yield: 72%, mp: 153 to 154° C.). FT-IR ($cm^{-1}$): 3399 (OH), 2973, 2927, 2906 (—$CH_2$—), 1693 (C=O in Ar—COO—), 1601, 1504 (C—C in Ar); $^1$H-NMR ($CDCl_3$, δ, ppm): 1.38 (t, 3H, $OCH_2CH_3$), 4.35 (q, 2H, $OCH_2CH_3$), 7.03-8.17 (m, 8H, aromatic)
FIG. 2 is an FT-IR spectrum of Intermediate 1.

Synthesis of ethyl 4-[4-(6-hydroxyhexyl)phenylazo]benzoate (Intermediate 2)

(1) 4-hydroxy-4-ethoxycarbonyl azobenzol (18.7 g, 69.3 mmol), which is Intermediate 1, is dissolved in EtOH (100 mL).

(2) KOH (4.3 g, 76.2 mmol) is dissolved in EtOH (100 mL), and then the solution in (1) is slowly added thereto.

(3) 1-cholo-6-hexenol (14.5 g, 103.9 mmol) and KI (3 g, 18.1 mmol) are added to the solution in (2), and the mixture is heated under reflux for 30 minutes. After the reaction, the product is extracted three times by using water (100 mL) and $CHCl_3$ (100 mL, divided into each 20 mL) to separate an organic layer.

Figure 3:
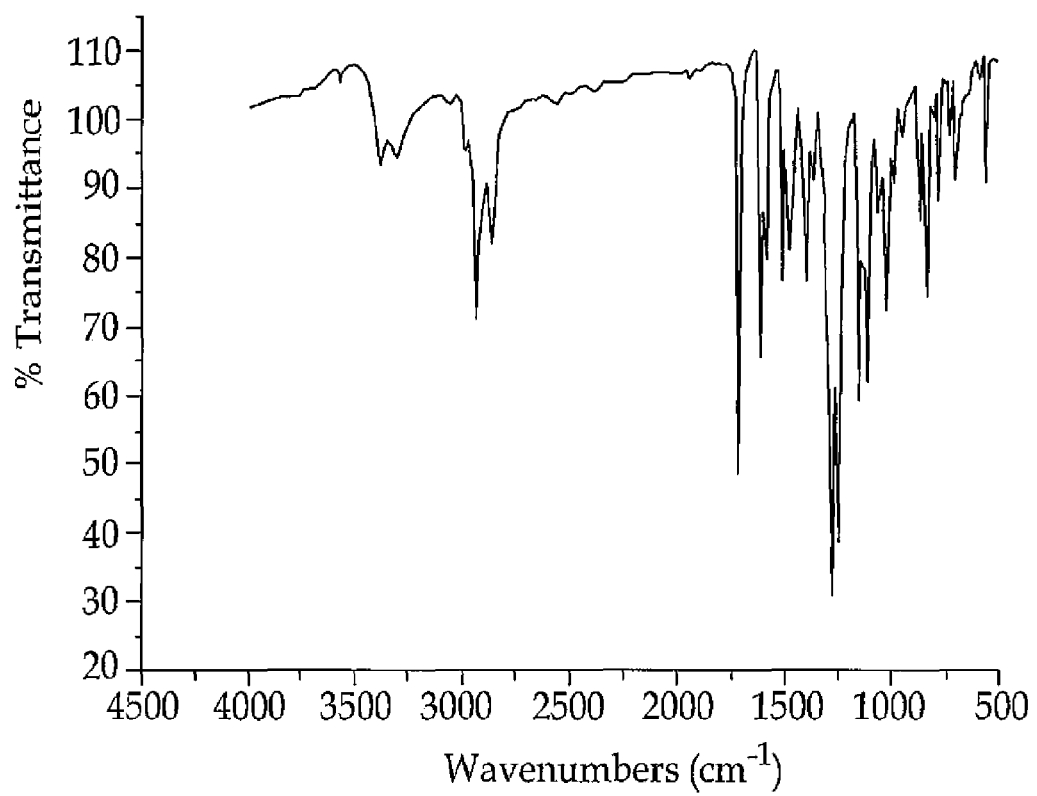
FIG. 3 is an FT-IR spectrum of Intermediate 2.

(4) The separated organic layer is dried over $Na_2SO_4$, and then a product obtained by removing the solvent by a rotary evaporation method is dried at 40° C. in a vacuum oven, and then is recrystallized twice from EtOH to obtain Intermediate 2. (19.5 g, yield: 76%, mp: 90-91° C.), FT-IR ($cm^{-1}$): 3357 (OH), 2940, 2864 (—$CH_2$—), 1706 (C=O in Ar—COO—), 1600, 1501 (C—C in Ar), 1260 (COC); $^1$H-NMR ($CDCl_3$, δ, ppm): 1.33-1.80 (m, 11H, methyl), 3.43 (t, 2H, $HOCH_2CH_2$), 4.13 (t, 2H, $OCH_2CH_2$), 4.39 (q, 2H, $OCH_2CH_3$), 7.04-8.18 (m, 8H, aromatic)
FIG. 3 is an FT-IR spectrum of Intermediate 2.

Synthesis of 4-[4-(6-hydroxyhexyloxy)phenylazo]benzoic acid (Intermediate 3)

(1) A slurry that is ethyl 4-[4-(6-hydroxyhexyl)phenylazo] benzoate (1.5 g, 4 mmol) and KOH (0.6 g, 10 mmol) are put into EtOH (300 mL) and distilled water (100 mL), and then the mixture is heated under reflux overnight.

(2) The above mixture is put into a 10-fold volume of acidic distilled water having a pH of 3 to perform precipitation.

(3) A slurry NaCl is added thereto to produce a yellow or orange suspended material on the surface of the aqueous solution, and then the solution is filtered under reduced pressure to obtain a solid. The obtained solid is washed with a large amount of water until the pH becomes about 7.

(4) The obtained product is dried at 40° C. in a vacuum oven for 2 days, recrystallized twice from MeOH, and then completely dried at 40° C. in a vacuum oven to obtain Intermediate 3 which is a bright orange crystal. (0.7 g, yield: 53%), FT-IR ($cm^{-1}$): 3318 (m), 2939 (s), 2854 (m), 2628 and 2502 (w, from H bonds between carboxylic groups), 1663 (s), 1600 (s), 1583 (s), 1501 (m), 1475 (m), 1418 (m), 1301 (m), 1254 (s), 1140 (s), 1113 (m), 1057 (w), 1024 (s), 920 (w), 865 (m), 840 (m), 781 (w), 725 (w); $^1$H-NMR (DMSO-d6, δ, ppm): 1.4-1.7 (m, 8H, methyl), 3.8 (t, 2H, $HOCH_2CH_2$), 4 (t, 2H, $OCH_2CH_2$), 7.1 (d, 2H, aromatic), 7.9 (dd, 4H, aromatic), 8.1 (d, 2H, aromatic)

Synthesis of 6-[4-(4-benzoic acidazo)phenoxy]-hexylmethacrylate (Intermediate 4)

(1) Dimethylamino pyridine (0.04 g, 0.3 mmol), methacrylic acid anhydride (1 g, 6.4 mmol), triethylamine (0.6 g, 6.32 mmol), and 4-[4-(6-hydroxyhexyloxy)phenylazobenzoic acid (1 g, 2.9 mmol) are put into THF (100 mL) to dissolve the mixture. When a dark red solution is formed, the solution is reacted at 40° C. for 48 hours.

(2) A product is dissolved in acetic acid at 120° C. and then n-hexane is added thereto until crystals begin to appear for the first time. When the crystal begins to be produced, the mixture is cooled to 5° C. and left to stand overnight, and then the solid is separated by a reduced-pressure filtration method.

(3) The obtained solid is dissolved in acetic acid at 120° C., the solution is cooled to normal temperature (for about 4 hours), stored at 5° C. overnight, and then filtered under reduced pressure to obtain a solid crystal.

(4) The obtained crystal is washed and then dried at 40° C. in a vacuum oven to obtain Intermediate 4 which is an orange powder. (0.9 g, yield: 76%), FT-IR ($cm^{-1}$): 2939 (s), 2867 (s), 2663 and 2548 (m, from H-bonds between carboxylic groups), 1782 (w), 1716 (s), 1680 (s), 1634 (w, C=C), 1602 (s), 1582 (m), 1502 (m), 1473 (m), 1420 (m), 1279 (s), 1250 (s), 1169 (s), 1141 (s), 1109 (w), 1015 (m), 944 (w), 867 (w), 849 (m), 811 (w), 777 (w); $^1$H-NMR ($CDCl_3$, δ, ppm): 1 to 2 (m, 11H, methyl), 4.1 (double t, 4H, $OCH_2CH_2$), 5.7 (m, 1H, vinyl), 6 (m, 1H, vinyl), 7.1 (d, 2H, aromatic), 7.9 (dd, 4H, aromatic), 8.1 (d, 2H, aromatic)

Synthesis of 4'-hexyloxyacetophenone (Intermediate 5)

(1) Sodium hydride (95%, 0.56 g) is slowly added to an aqueous solution prepared by dissolving 4'-hydroxyacetophenone (3 g, 22.03 mmol) in THF (100 mL), and the mixture is reacted in a nitrogen atmosphere for 2 hours.

(2) After the reaction, the produced sodium salt precipitate is filtered under reduced pressure, and then dissolved in methanol (50 mL).

(3) 1-bromohexane (3.71 mL, 26.44 mmol) is added to the mixture, and heated under reflux in a nitrogen atmosphere for 24 hours.

(4) The product is passed through a silica gel column (5 cm) filled with ethyl acetate to remove the precipitate.

(5) The obtained liquid mixture is dried under reduced pressure, and then separated by a column chromatography (silica gel, 20% ethyl acetate in hexane) method to obtain Intermediate 5. (3 g, yield: 62%), FT-IR (cm$^{-1}$): 3338, 3072, 2935, 2858, 1679, 1604, 1512, 1423, 1361, 1255, 1179 $^1$H-NMR (CDCl$_3$, 6, ppm): 7.95-6.85 (dd, 4H, aromatic proton), 4 (t, 2H, —OCH$_2$—), 2.55 (s, 3H, CH$_3$CO—), 1.9-0.85 (m, 11H, alkyl proton)

Figure 4:
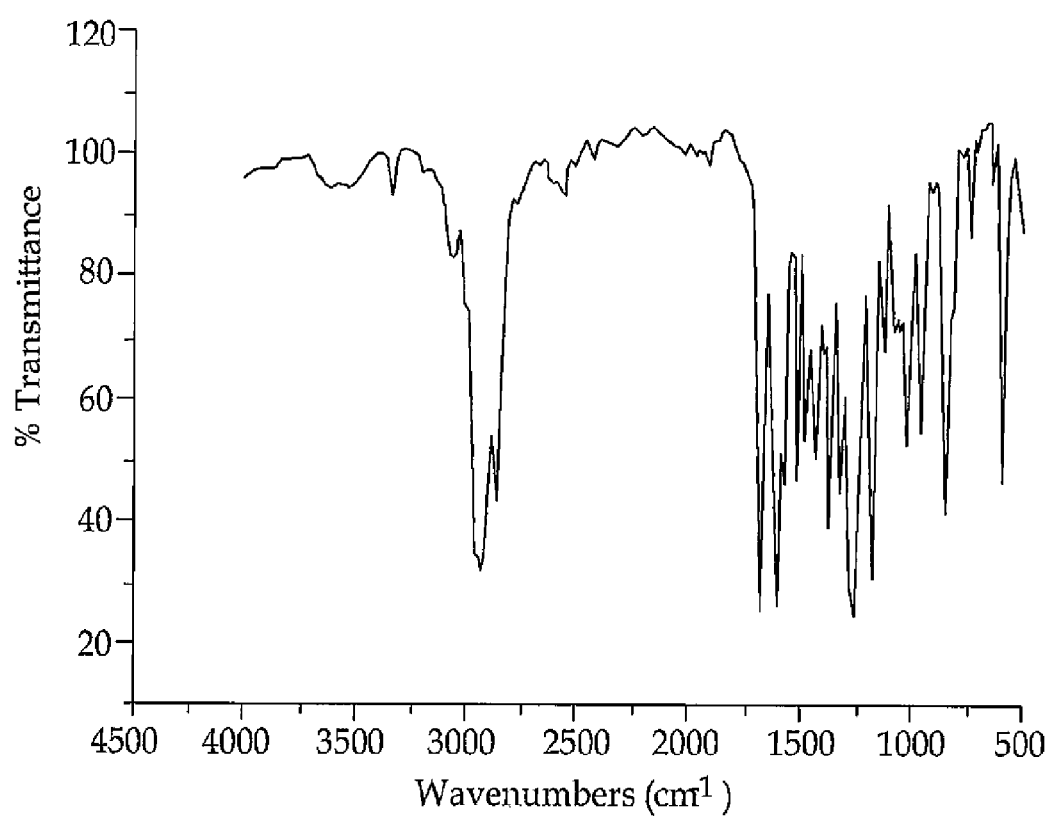
FIG. 4 is an FT-IR spectrum of Intermediate 5.

FIG. 4 is an FT-IR spectrum of Intermediate 5.

Synthesis of 4-hydroxy-4'-hexyloxychalcone (Intermediate 6)

(1) 4'-hexyloxyacetophenone (2.99 g, 13.57 mmol) and sulfuric acid (98%, 3 mL) are added to a solution prepared by dissolving 4-hydroxybenzaldehyde (1.66 g, 13.57 mmol) in acetic acid (100 mL).

(2) The solution is stirred at normal temperature in a nitrogen atmosphere for 22 hours, and then the aqueous solution is neutralized with a 5 N NaOH aqueous solution to perform precipitation.

(3) A solid obtained by filtering the precipitate under reduced pressure is separated and purified by a column chromatography (silica gel, 33% ethyl acetate in hexane) method, and then recrystallized with ethyl acetate/hexane to obtain Intermediate 6. (3.08 g, yield: 70%), FT-IR (cm$^{-1}$): 3211, 2937, 2866, 1641, 1603, 1506, 1225, 1167; $^1$H-NMR (CDCl$_3$, δ, ppm): 8.1-6.85 (dddd, 8H, aromatic proton), 7.8, 7.4 (q, 2H, vinyl proton), 6 (s, 1H, —OH), 4 (t, 2H, —OCH$_2$—), 1.9-0.85 (m, 11H, alkyl proton)

Figure 5:
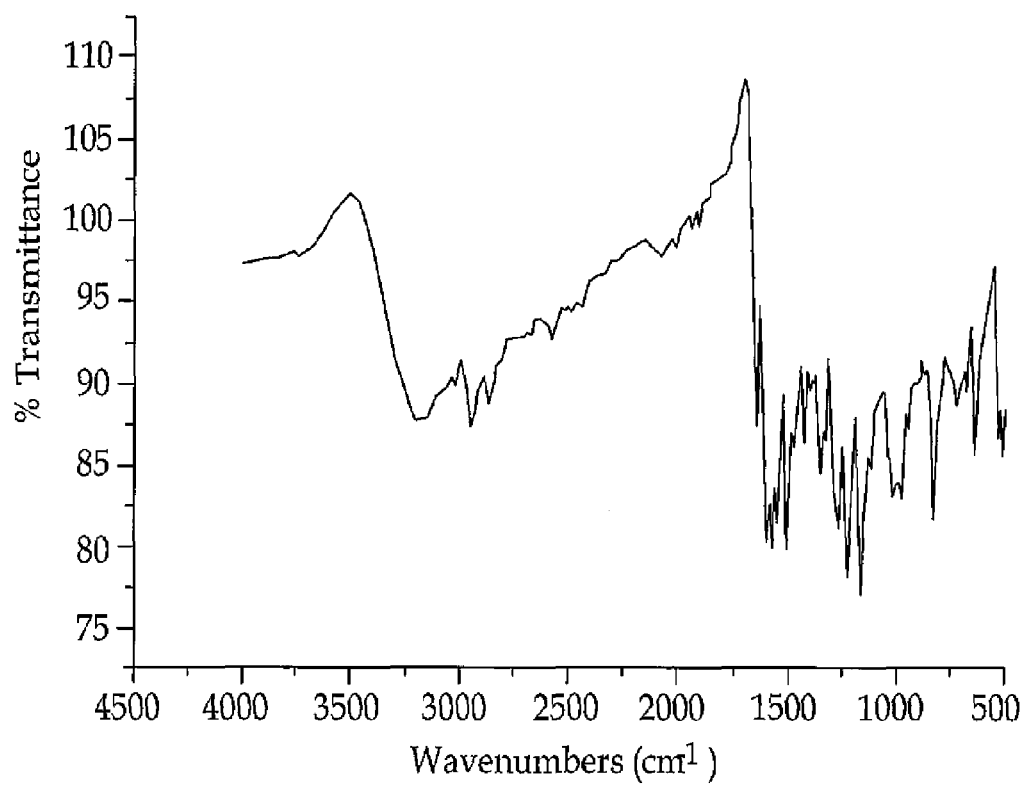
FIG. 5 is an FT-IR spectrum of Intermediate 6.

FIG. 5 is an FT-IR spectrum of Intermediate 6.

Preparation of 6-[4'-(4-hexyloxychalconyl benzoate azo)phenoxy]-hexylmethacrylate (Compound Represented by Formula 6b)

(1) 6-[4-(4-benzoic acidazo)phenoxy]-hexylmethacrylate (1.85 g, 4.5 mmol) is dissolved in distilled THF (50 mL) in an argon atmosphere.

(2) COCl$_2$ (0.81 mL, 9.5 mmol) is slowly added to the aqueous solution in (1) by a syringe, three drops of DMF are added thereto by a syringe, the mixture is reacted for 2 hours, and then the solvent is totally removed by a rotary evaporator.

(3) 4-hydroxy-4'-hexyloxychalcone (1.76 g, 5.4 mmol) is put into distilled THF (17 mL) to perform dilution, and then TEA (1.25 mL, 5.4 mmol) is slowly injected thereto in an argon atmosphere by a syringe.

(4) The reactant in (2) is diluted with the dried THF (33 mL), slowly added to the mixture in (3), and then stirred at ordinary temperature for 15 hours.

(5) The reactant is put into a mixture of distilled water and dichloromethane and extracted three times to separate an organic layer, and then the solvent is dried under reduced pressure and totally removed.

(6) A product obtained in (5) is separated and purified by a column chromatography (silica gel, ethyl acetate/hexane/ MC, 1:20:20) method to obtain a compound represented by Formula 6b which is an orange solid. Product (3.06 g, yield: 95%), FT-IR (cm$^{-1}$): 2939 (s), 2865 (s), 1734 (w), 1716 (s), 1654 (s), 1602 (w, C=C), 1501 (m), 1418 (m), 1164 (s), 1141 (s), 1109 (w), 1015 (m), 833 (w); $^1$H-NMR (CDCl$_3$, 6, ppm): 1-2 (m, 21H, methyl), 4.1 (double t, 4H, OCH$_2$CH$_2$), 4.2 (t, 2H, OCH$_2$CH$_2$), 5.6 (m, 1H, vinyl), 6.2 (m, 1H, vinyl), 7.1 (dd, 4H, aromatic), 7.9 (dd, 4H, aromatic), 8.4 (d. 2H, aromatic)

Figure 6:
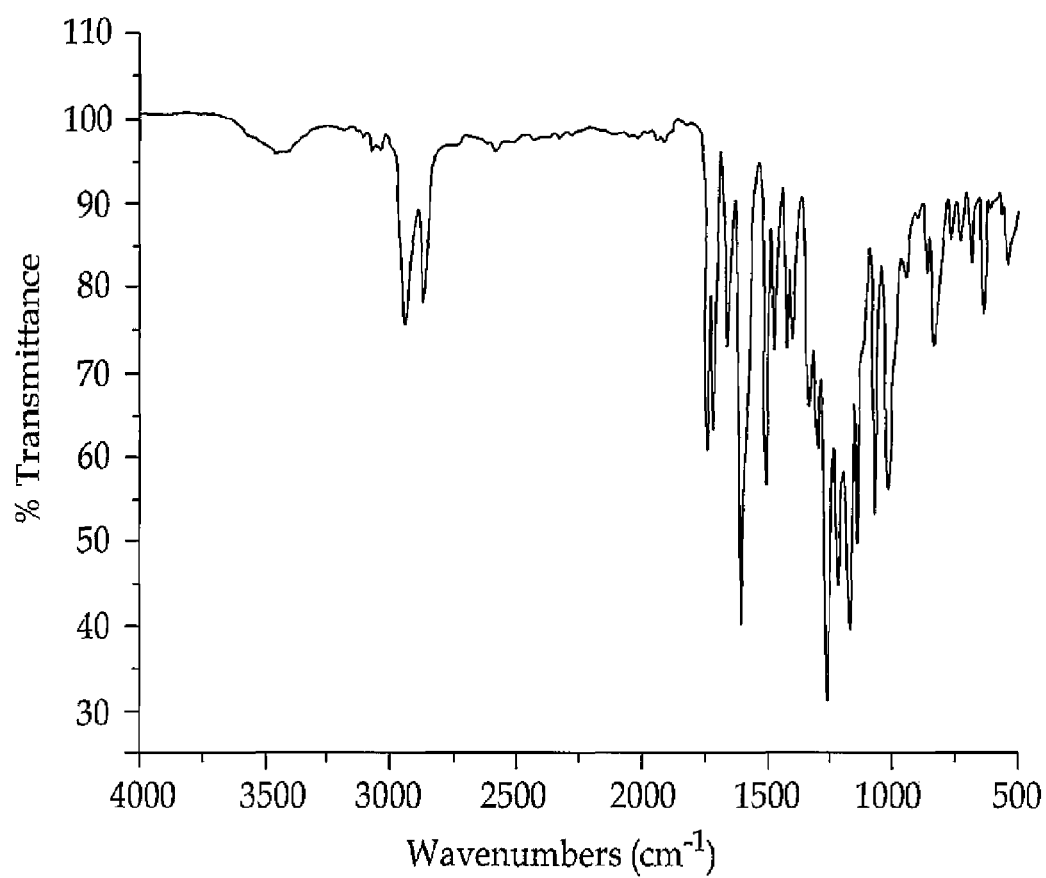
FIG. 6 is an FT-IR spectrum of Intermediate 7.

FIG. 6 is an FT-IR spectrum of the compound represented by Formula 6b.

Example 2

Preparation of Polymer Represented by Formula 8

First, benzoyl peroxide (BPO) as a polymerization initiator was purchased from Acros Corp., and recrystallized from chloroform/methanol (1:1, v/v). Anhydrous benzene as a solvent was purchased from Aldrich Chemical Co., and directly used without any purification.

6-[4'-(4-hexyloxychalconyl benzoate azo)phenoxy]-hexylmethacrylate (compound of Formula 6b) and benzoyl peroxide (5% by mol) were put into an ampule and anhydrous benzene was added thereto to dissolve the mixture. Gas was completely removed from the ampule into which the mixture was put by repeating a freeze-degas-thaw method four times using liquid nitrogen and a high vacuum pump, and then a gas torch was used under vacuum to seal the ampule. The mixture was left to stand until normal temperature was reached, and was allowed to undergo polymerization reaction at 80° C. for 24 hours.

After 24 hours, the reactant was cooled to 0° C. in order to complete the polymerization reaction, and then was precipitated in excess of hot methanol. The produced precipitate was filtered, washed several times with hot methanol, and then dried at normal temperature in a vacuum oven for 24 hours to obtain a pale orange polymer represented by Formula 2.

Figure 7:
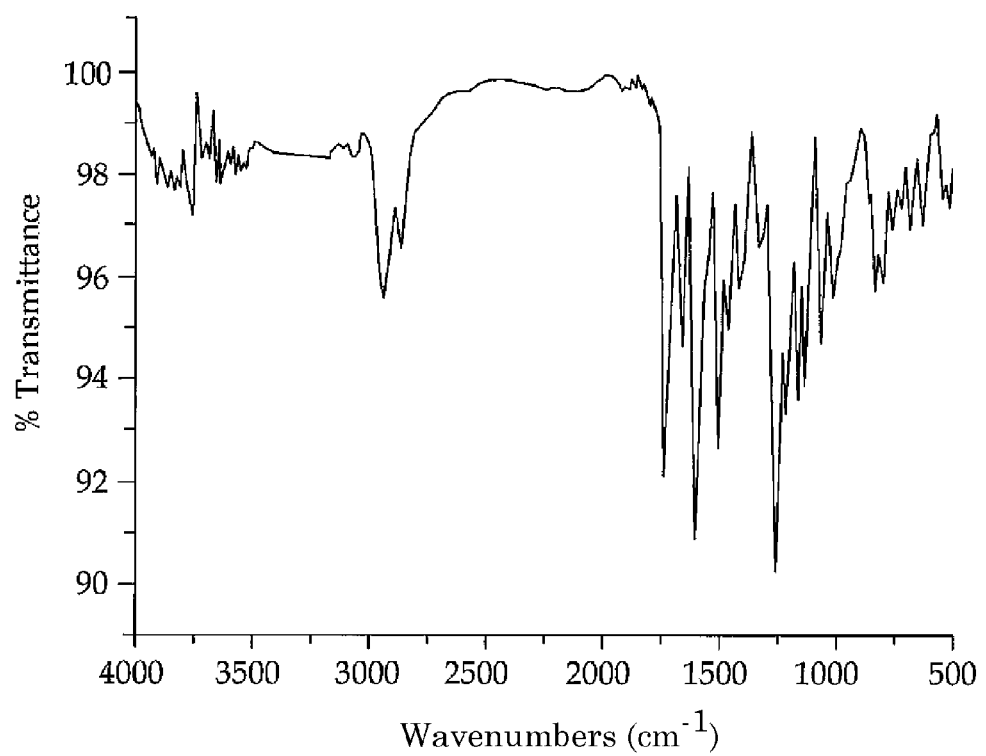
FIG. 7 is an FT-IR spectrum of the polymer.

FIG. 7 is an FT-IR spectrum of the polymer represented by Formula 8.

Test Example 1

Evaluation of Heat Characteristics

Figure 8:
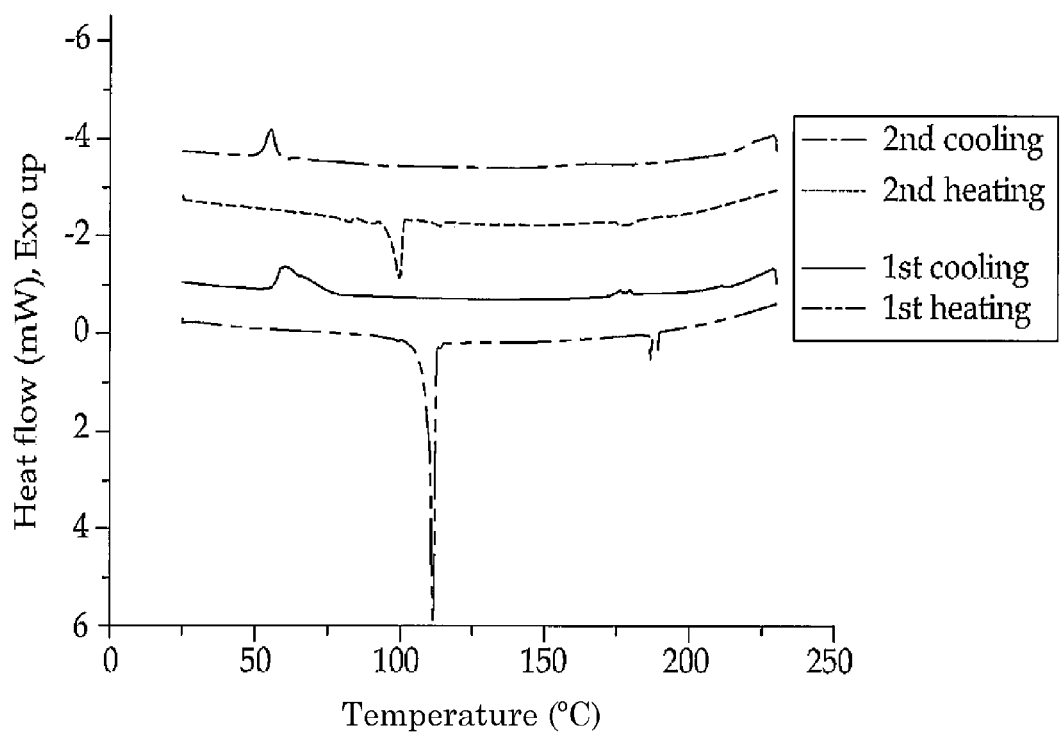
FIGS. 8 and 9 are results obtained by measuring heat characteristics of a compound prepared in Example 1 and a polymer prepared in Example 2, respectively.
Figure 9:
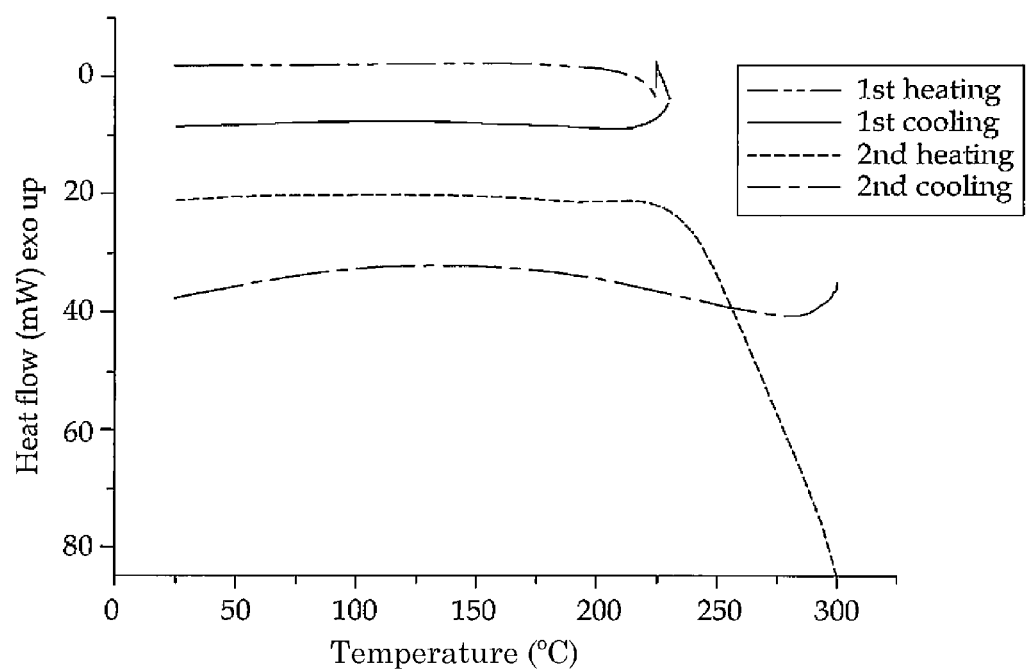

DSC results obtained by measuring heat characteristics of the compound prepared in Example 1 and the polymer prepared in Example 2 are shown in FIGS. 8 and 9.

As shown in FIGS. 8 and 9, the compound and the polymer according to the present invention show characteristics of nematic thermotropic liquid crystal that has liquid crystal characteristics in response to heat, and thus the interaction with liquid crystal is excellent compared to compounds or polymers which are used in an alignment film in the related art. In addition, compounds which are not a polymer have liquid crystal characteristics alone and thus may be applied to various fields. Accordingly, the optical film according to the present invention may be usefully applied particularly to liquid crystal display devices (LCD).

What is claimed is:

1. A compound represented by the following Formula 1:

[Formula 1]

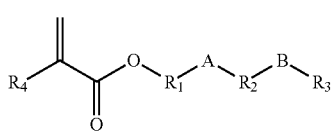

wherein each of A and B is one of substituents represented by the following Formula 2a and the following Formula 3a such that both A and B are not substituents represented by the Formula 2a at the same time,

[Formula 2a]

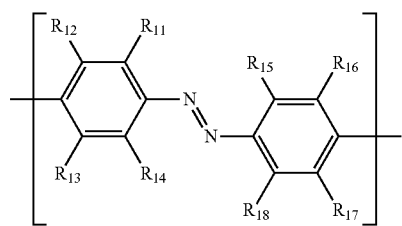

[Formula 3a]

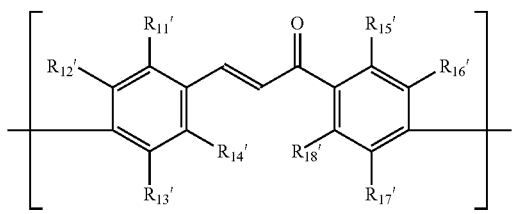

$R_{11}$ to $R_{18}$ and $R_{11}'$ to $R_{18}'$ may be the same as or different from each other, and are each selected from the group consisting of hydrogen (H), an alkyl group having from 1 to 20 carbon atoms, an alkoxy group having from 1 to 20 carbon atoms, an aryl group and an alkyl ester group having from 1 to 20 carbon atoms;

$R_1$, $R_2$ and $R_3$ may be the same as or different from each other, and are each selected from the group consisting of an alkyl group having from 1 to 20 carbon atoms, an alkoxy group having from 1 to 20 carbon atoms, an aryl group and an alkyl ester group having from 1 to 20 carbon atoms, and $R_4$ is H or $CH_3$.

2. The compound as claimed in claim 1, wherein the compound represented by Formula 1 is represented by the following Formula 4 or Formula 5:

[Formula 4]

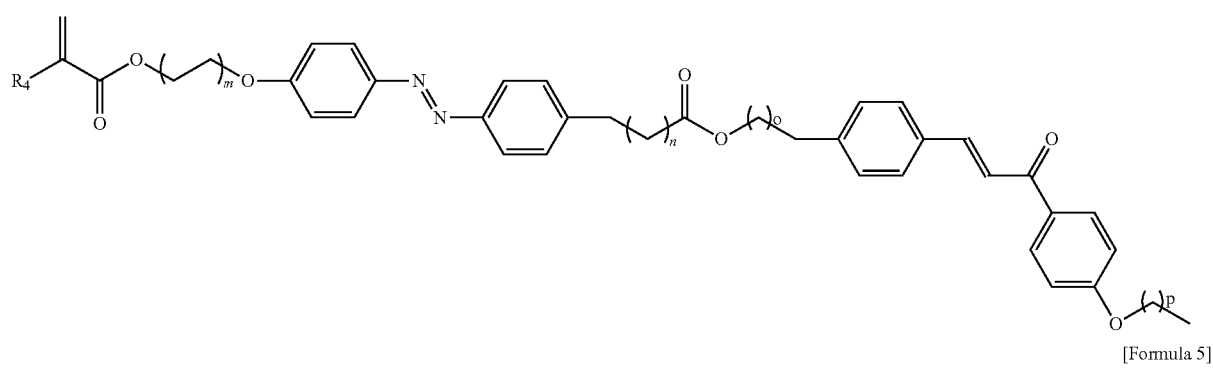

[Formula 5]

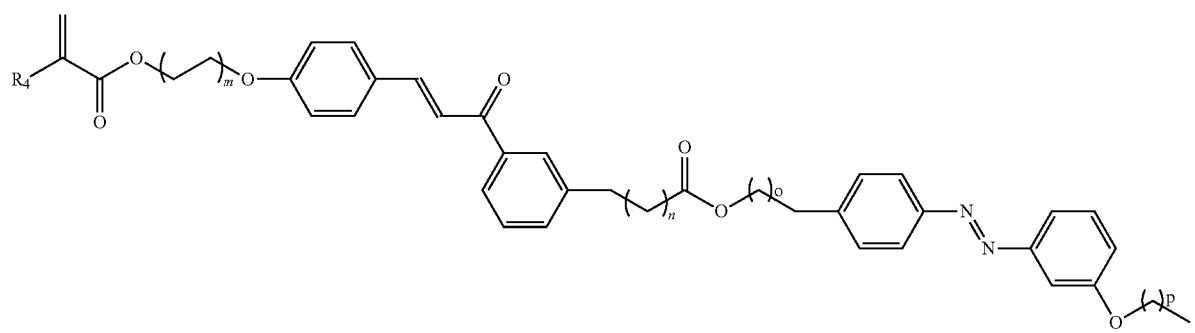

wherein m, n, o and p are each an integer from 1 to 5, and R₄ is H or CH₃.

3. The compound as claimed in claim 1, wherein the compound represented by Formula 1 is a compound represented by the following Formula 6a or 6b:

[Formula 6a]

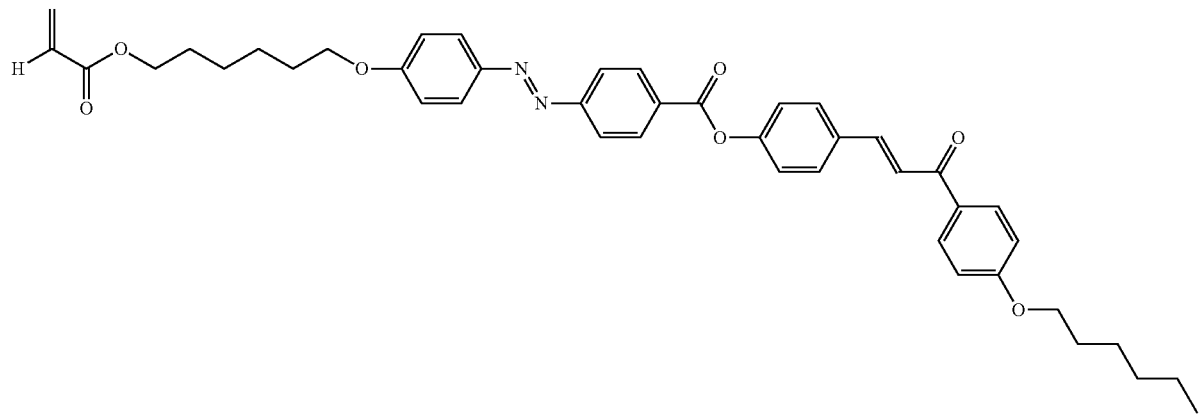

[Formula 6b]

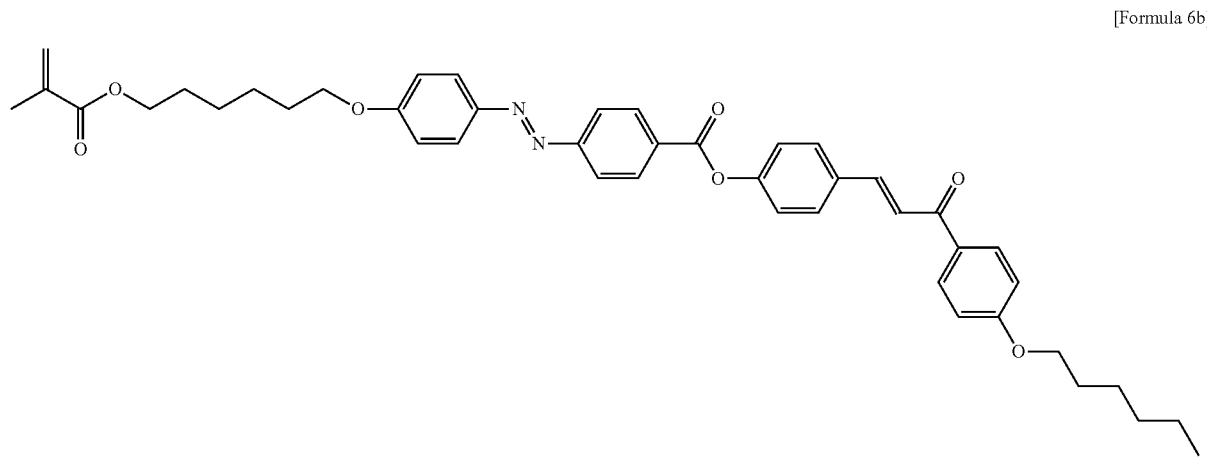

4. The compound as claimed in claim 1, wherein the compound absorbs light having at least one of wavelengths from 280 nm to 340 nm, from 345 nm to 380 nm and from 400 nm to 460 nm.

5. The compound as claimed in claim 1, wherein cycloaddition is generated by irradiation of light having a wavelength from 280 nm to 340 nm.

6. The compound as claimed in claim 1, wherein the compound is isomerized by irradiation of light having a wavelength from 345 nm to 380 nm or from 400 nm to 460 nm.

7. A polymer formed by polymerizing a monomer comprising the compound represented by Formula 1 as claimed in to claim 1.

8. The polymer as claimed in claim 7, wherein the monomer further comprises at least one or more of acrylic acid, methacrylic acid, acrylonitrile and styrene.

9. The polymer as claimed in claim 7, wherein the polymer is a homopolymer formed by a single monomer.

10. The polymer as claimed in claim 9, wherein the homopolymer is represented by the following Formula 7:

[Formula 7]

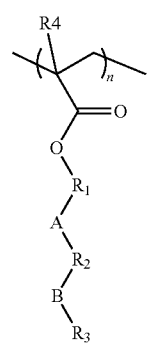

wherein A, B and R₁ to R₄ are the same as those as defined in claim 1, and n is an integer from 5 to 500.

11. The polymer as claimed in claim 7, wherein the polymer is a copolymer formed by two or more monomers different from each other.

12. The polymer as claimed in claim 11, wherein the copolymer is represented by the following Formula 10:

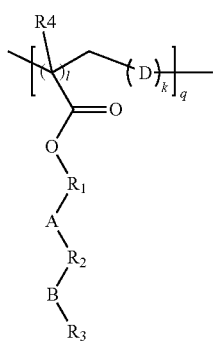

[Formula 10]

wherein A, B and $R_1$ to $R_4$ are the same as those as defined in claim 1,

D is at least one selected from the group consisting of methyl acrylate (MA), methyl methacrylate (MMA), acrylonitrile and styrene, and l and k are an integer from 1 to 100, and q is an integer from 5 to 500.

13. The polymer as claimed in claim 7, wherein the polymer has a molecular weight from 3,000 to 300,000.

14. An optical film comprising:
a film substrate; and
a coating layer formed by coating the polymer as claimed in claim 7 on a surface of the film substrate.

15. The optical film as claimed in claim 14, wherein the film substrate is selected from the group consisting of a polyacrylate (PA) film, a polymethylacrylate (PMA) film, a PMMA film, a PET film, a PC film, a PES film, a cyclic olefin compound (COC) film and a polyimide film.

16. The optical film as claimed in claim 14, wherein the coating layer forms an alignment film.

17. The optical film as claimed in claim 14, which is used as any one of a retardation film, a viewing angle compensation film and a protective film.

18. A method for preparing an optical film, comprising:
preparing a film substrate;
coating the polymer as claimed in claim 7 on one side of the film substrate; and
aligning the polymer by irradiating light.

19. The method as claimed in claim 18, wherein in the aligning of the polymer, light having at least one of wavelengths from 280 nm to 340 nm, from 345 nm to 380 nm and from 400 nm to 460 nm is irradiated.

20. A display device comprising the optical film as claimed in claim 14.

21. The display device as claimed in claim 20, wherein a pretilt angle defined as an angle between a substrate surface and liquid crystal molecules is selectable and controllable in a range of 3° or less for a horizontal alignment film and in a range of 80° or more for a vertical alignment film.

* * * * *